(12) United States Patent
Verhaak

(10) Patent No.: US 8,969,602 B2
(45) Date of Patent: Mar. 3, 2015

(54) PROCESS FOR THE PRODUCTION OF ETHYLENE OXIDE

(75) Inventor: Michael Johannes Franciscus Maria Verhaak, Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 13/981,144

(22) PCT Filed: Jan. 23, 2012

(86) PCT No.: PCT/EP2012/050923
§ 371 (c)(1),
(2), (4) Date: Sep. 30, 2013

(87) PCT Pub. No.: WO2012/101069
PCT Pub. Date: Aug. 2, 2012

(65) Prior Publication Data
US 2014/0018557 A1    Jan. 16, 2014

(30) Foreign Application Priority Data

Jan. 24, 2011 (EP) .................................... 11151794

(51) Int. Cl.
| | | |
|---|---|---|
| *C07D 301/03* | (2006.01) | |
| *C07C 29/00* | (2006.01) | |
| *C07C 31/18* | (2006.01) | |
| *C07D 301/10* | (2006.01) | |
| *C07C 29/132* | (2006.01) | |

(52) U.S. Cl.
CPC ............ *C07D 301/10* (2013.01); *C07C 29/132* (2013.01)
USPC ............ 549/523; 549/536; 568/852; 568/867

(58) Field of Classification Search
CPC ........ C07C 5/48; C07C 11/04; C07C 51/215; C07C 53/08; C07C 31/202; C07C 29/132; C07D 301/00; C07D 301/04; C07D 301/08; C07D 301/10
USPC ........................... 549/523, 536; 568/852, 867
See application file for complete search history.

(56) References Cited

U.S. PATENT DOCUMENTS

| | | |
|---|---|---|
| 709,137 A | 9/1902 | Chalfant |
| 4,990,632 A | 2/1991 | Ramachandran et al. |
| 5,990,369 A | 11/1999 | Barger et al. |
| 6,518,476 B1 * | 2/2003 | Culp et al. ..................... 585/655 |

(Continued)

FOREIGN PATENT DOCUMENTS

| | | |
|---|---|---|
| CN | 1041591 | 4/1990 |
| CN | 1215041 | 4/1999 |

(Continued)

OTHER PUBLICATIONS

U.S. Appl. No. 13/980,927, filed Sep. 2013, Verhaak.*

(Continued)

*Primary Examiner* — T. Victor Oh

(57) ABSTRACT

The invention relates to a process for the production of ethylene oxide, comprising the steps of producing ethylene resulting in a stream comprising ethylene and ethane; producing ethylene oxide by subjecting ethylene and ethane from the stream comprising ethylene and ethane to oxidation conditions resulting in a stream comprising ethylene oxide, unconverted ethylene and ethane; and recovering ethylene oxide from the stream comprising ethylene oxide, unconverted ethylene and ethane.

6 Claims, 3 Drawing Sheets

(56) References Cited

U.S. PATENT DOCUMENTS

| | | |
|---|---|---|
| 7,132,580 B1 | 11/2006 | Senetar |
| 7,504,545 B2 | 3/2009 | Boele et al. |
| 2004/0224841 A1 | 11/2004 | Matusz |
| 2004/0225138 A1 | 11/2004 | McAllister et al. |
| 2004/0247393 A1 | 12/2004 | Hess et al. |
| 2006/0020083 A1 | 1/2006 | Yumamoto et al. |
| 2007/0155999 A1 | 7/2007 | Pujado et al. |
| 2007/0203380 A1 | 8/2007 | Vora et al. |
| 2008/0139853 A1 | 6/2008 | Boele et al. |
| 2008/0182999 A1 | 7/2008 | Rekers et al. |
| 2009/0234144 A1 | 9/2009 | Bos et al. |
| 2009/0281345 A1 | 11/2009 | Matusz |
| 2010/0256432 A1 | 10/2010 | Arnold et al. |
| 2011/0009653 A1* | 1/2011 | Mazanec et al. ............... 549/536 |

FOREIGN PATENT DOCUMENTS

| | | |
|---|---|---|
| CN | 1237481 | 12/1999 |
| CN | 1269341 | 10/2000 |
| CN | 1463960 | 12/2003 |
| CN | 101362669 | 2/2009 |
| EP | 0850936 | 7/1998 |
| GB | 1213483 | 11/1970 |
| GB | 1314613 | 4/1973 |
| WO | 0236532 | 5/2002 |
| WO | 03064035 | 8/2003 |
| WO | 2006020083 | 2/2006 |
| WO | 2007135052 | 11/2007 |
| WO | 2009065848 | 5/2009 |
| WO | 2009065855 | 5/2009 |
| WO | 2009065870 | 5/2009 |
| WO | 2009065875 | 5/2009 |
| WO | 2009065877 | 5/2009 |
| WO | 2010096909 | 9/2010 |
| WO | 20110057976 | 5/2011 |
| WO | 20110057980 | 5/2011 |

OTHER PUBLICATIONS

Kobe, J.M. et al; "Epoxidation-Homogeneous"; Encyclopedia of Catalysis; 2003, vol. 3; pp. 246-248.

Kniel et al., "Ethylene, Keystone to the Petrochemical Industry", Chapter 6, Manufacture & Chapter 7, The Modern Ethylene Plant; SPE papers 100089 (UT) & 99744-PA-P (Rice Univ), 1980, pp. 62-108.

* cited by examiner

PROCESS FOR THE PRODUCTION OF ETHYLENE OXIDE

PRIORITY CLAIM

The present application claims priority from PCT/EP2012/050923, filed 23 Jan. 2012, which claims priority from European application 11151794.2, filed 24, Jan. 2011, which are incorporated herein by reference.

BACKGROUND TO THE INVENTION

The present invention relates to a process for the production of ethylene oxide.

Ethylene oxide is used as a chemical intermediate, primarily for the production of ethylene glycols but also for the production of ethoxylates, ethanol-amines, solvents and glycol ethers. It is produced by the direct oxidation of ethylene with high-purity oxygen or air. Several processes for producing the ethylene starting material are known. For example, it is known to steam crack hydrocarbon streams, such as an ethane stream, a naphtha stream, a gasoil stream or a hydrowax stream, into ethylene. Further, it is known to produce ethylene by oxidative dehydrogenation (oxydehydrogenation; ODH) of ethane. Yet another way to produce ethylene is by conversion of an oxygenate, such as methanol, into ethylene.

All these ethylene production processes have in common that before any subsequent step wherein the ethylene is further converted into useful chemical intermediates, the ethylene containing product stream has to be purified. For example, the ethylene containing product stream has to be freed from ethane as the latter may interfere in any subsequent step, so that a purified ethylene stream can be fed to the subsequent step, such as the step of oxidation of ethylene. Said ethane may originate from the feed for producing the ethylene. For example, the above-mentioned ethane steam cracking and ethane oxydehydrogenation processes may result in product streams which still contain unconverted ethane in addition to the desired ethylene product. Further, such ethane may originate from ethylene production processes wherein ethane is produced as a by-product. For example, in the above-mentioned naphtha, gasoil or hydrowax steam cracking and methanol to ethylene conversion processes, ethane is produced as a by-product. Separating ethane from an ethylene product stream may be done by use of an ethylene/ethane splitter. Having to separate ethane from the ethylene is very cumbersome and results in a high expenditure for producing ethylene and results in relatively high ethylene losses.

Further, in case said purified ethylene stream not containing ethane is used to make ethylene oxide by oxidation, a ballast gas should be added. For in the oxidation of ethylene an oxidizing agent, such as high-purity oxygen or air, is required. In 1958, the direct ethylene oxidation process was modified by Shell to allow the use of high-purity oxygen, rather than air, as the oxidant. See: J. M. Kobe, W. E. Evans, R. L. June, and M. F. Lemanski, Encyclopedia of Catalysis, Istvan Horvath, Ed., Wiley-Interscience, v. 3, p. 246, 2003.

Because an oxidizing agent is required, it is important to control the safe operability of the reaction mixture. Historically, nitrogen was utilized as a ballast gas for the industrial epoxidation of ethylene. Over the past thirty years, the use of methane ballast has gradually replaced almost all commercial nitrogen-ballasted processes. One function of a ballast gas is thus to control this safe operability. Ballast gases that can be used in the production of ethylene oxide by oxidation of ethylene, are thus nitrogen and methane. It is very cumbersome to provide such ballast gas and feed it to the ethylene oxidation unit, which results in a high expenditure for producing ethylene oxide.

An object of the present invention is to provide a process for the production of ethylene oxide by producing ethylene and then producing ethylene oxide by oxidation of said ethylene, which process does not have the above drawbacks.

SUMMARY OF THE INVENTION

Surprisingly, it was found that the above drawbacks are avoided by means of an integrated process wherein ethylene is produced resulting in a stream comprising ethylene and ethane, wherein ethylene and ethane from the latter stream are subjected to oxidation conditions resulting in the desired ethylene oxide Accordingly, the present invention relates to a process for the production of ethylene oxide, comprising the steps of:

producing ethylene resulting in a stream comprising ethylene and ethane;

producing ethylene oxide by subjecting ethylene and ethane from the stream comprising ethylene and ethane to oxidation conditions resulting in a stream comprising ethylene oxide, unconverted ethylene and ethane; and recovering ethylene oxide from the stream comprising ethylene oxide, unconverted ethylene and ethane.

An advantage of the present invention is that no ethane has to be separated from the ethylene containing product stream that results from the ethylene production step. This results in a much simpler overall process using less separation processes and equipment. In addition, the non-separated ethane advantageously functions as a ballast gas in the next ethylene oxidation step so that no or substantially less additional ballast gas needs to be added. Still further, separation of the stream comprising ethylene and ethane resulting from the ethylene production step of the present process is advantageously automatically, and at least partially, effected in the ethylene oxide production step wherein the ethylene is consumed and converted into ethylene oxide which can be separated more easily from the non-consumed ethane. All these and other advantages result in a substantial reduction of expenditure, for example savings on costs for compression, refrigeration, etc. needed for separating ethane from the ethylene. These and other advantages are further described below.

DETAILED DESCRIPTION OF THE INVENTION

Figure 1:
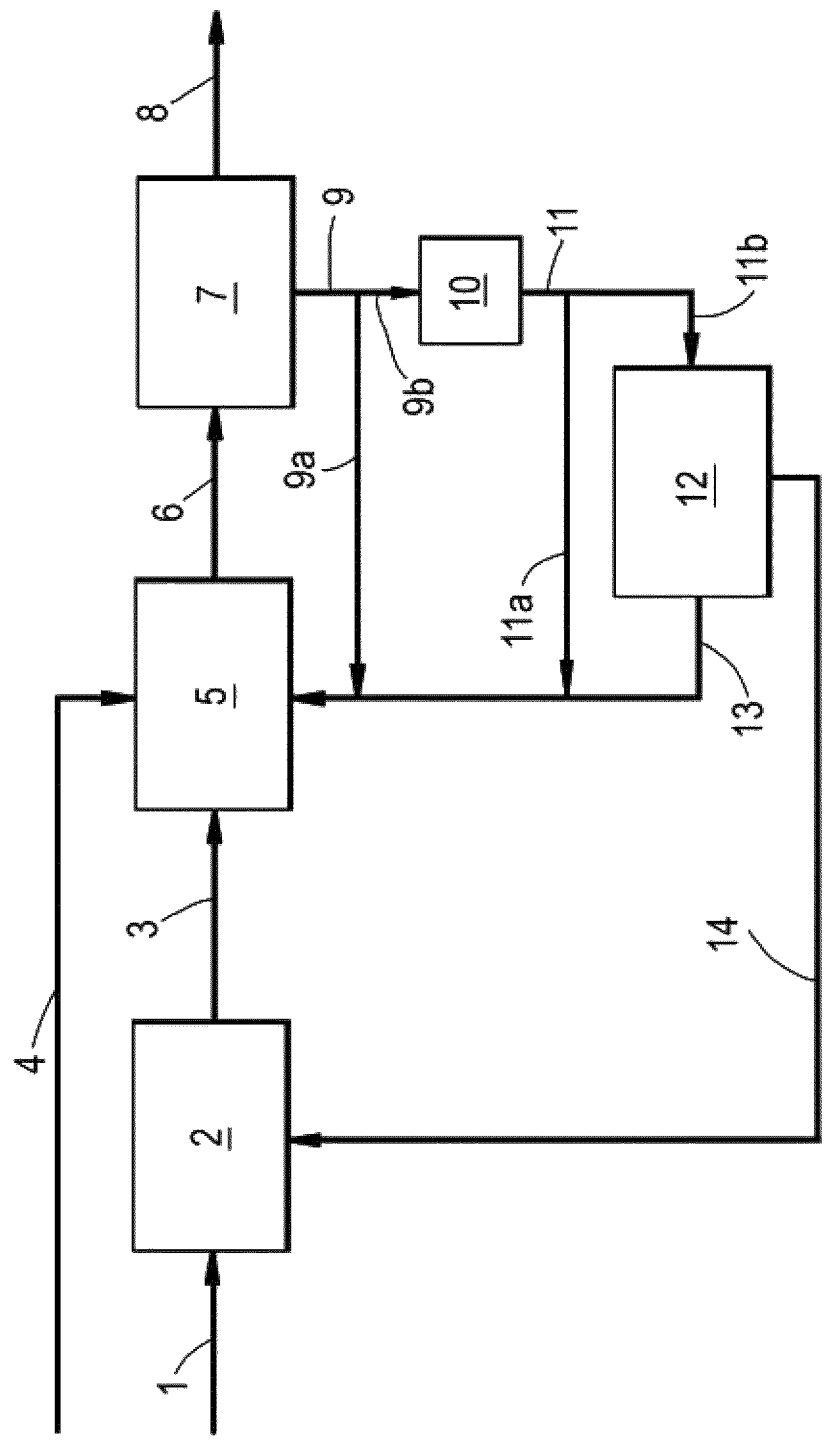
FIG. 1 shows a schematic representation of an embodiment of the process according to the invention.

GB1314613 discloses the use of ethane as a ballast gas in the production of ethylene oxide from ethylene. However, the integrated process of the present invention is not disclosed and is neither suggested in GB1314613.

The ethylene oxidation step in the present process results in a stream comprising ethylene oxide, unconverted ethylene and ethane. The ethylene oxide can be recovered easily from such stream by means of methods known to the skilled person. That is to say, ethylene oxide may be separated from said stream comprising ethylene oxide, unconverted ethylene and ethane resulting in a stream comprising unconverted ethylene and ethane. The unconverted ethylene and the ethane from the latter stream may be recycled within the present process and advantageously be converted and re-used, respectively, after such recycle. After ethylene oxide is separated from said stream comprising ethylene oxide, unconverted ethylene and ethane and before such recycle of the remaining unconverted ethylene and ethane, any carbon dioxide is removed. That is to say, either part or all carbon dioxide is removed. Said carbon dioxide may be produced in the ethylene oxide production step. Ways of removing carbon dioxide, such as a caustic wash, are known to the skilled person.

Unconverted ethylene, and optionally ethane, from the stream comprising ethylene oxide, unconverted ethylene and ethane resulting from the step of producing ethylene oxide may be recycled to that step of producing ethylene oxide. That is to say, either part or all unconverted ethylene, and optionally ethane, is recycled in such way. The recycled unconverted ethylene is then advantageously converted as yet in that ethylene oxidation step. Further, the recycled ethane is then advantageously re-used as a ballast gas in that ethylene oxidation step. In this embodiment, preferably, a stream comprising unconverted ethylene and ethane is separated from the stream comprising ethylene oxide, unconverted ethylene and ethane resulting from the step of producing ethylene oxide, and is then recycled to the step of producing ethylene oxide. Such recycle has both said advantages in that conversion of unconverted ethylene into ethylene oxide is effected as yet, whereas re-use of ethane as a ballast gas is also effected at the same time.

In cases wherein ethylene is produced from a feed containing ethane in the ethylene production step of the present process, ethane from the stream comprising ethylene oxide, unconverted ethylene and ethane resulting from the step of producing ethylene oxide may also be recycled to the ethylene production step. In the latter embodiment, ethane from the stream comprising ethylene oxide, unconverted ethylene and ethane is recycled to the step of producing ethylene. That is to say, either part or all ethane is recycled in such way. This embodiment has the advantage that more ethylene may be produced by recycling unconverted ethane whereas ethane that is still not converted after such recycle will then automatically be re-used as a ballast gas in the ethylene oxidation step.

Further, in such cases wherein ethylene is produced from a feed containing ethane in the ethylene production step of the present process, ethane from the stream comprising ethylene oxide, unconverted ethylene and ethane resulting from the step of producing ethylene oxide may also be recycled to both the ethylene production step and the ethylene oxide production step. In the latter embodiment, ethane from the stream comprising ethylene oxide, unconverted ethylene and ethane is recycled to the step of producing ethylene and to the step of producing ethylene oxide. This embodiment is illustrated in FIG. 1.

Where in the present specification reference is made to recycling to the "step of producing ethylene" or "ethylene production step", or recycling to the "step of producing ethylene oxide", "ethylene oxide production step" or "ethylene oxidation step", such steps not only cover the step(s) of production of the desired product in question but also the step(s) of work-up of the product stream in question.

In the flow scheme of FIG. 1, stream 1 comprising a feed containing ethane is fed to ethylene production unit 2. Stream 3 comprising ethylene and ethane and stream 4 comprising an oxidizing agent, such as high-purity oxygen or air, are fed to ethylene oxide production unit 5. Stream 6 comprising ethylene oxide, unconverted ethylene, ethane and carbon dioxide is sent to ethylene oxide separation unit 7. Ethylene oxide is recovered via stream 8. Further, stream 9 comprising unconverted ethylene, ethane and carbon dioxide is split into two substreams 9a and 9b. Substream 9a is recycled to ethylene oxide production unit 5. Substream 9b is fed to carbon dioxide removal unit 10. Stream 11 comprising unconverted ethylene and ethane is split into two substreams 11a and 11b. Substream 11a is recycled to ethylene oxide production unit 5. Substream 11b is fed to ethylene/ethane separation unit 12. Stream 13 comprising unconverted ethylene and stream 14 comprising unconverted ethane are recycled to ethylene oxide production unit 5 and to ethylene production unit 2, respectively. Further, a third stream may be separated in ethylene/ethane separation unit 12, namely a top bleed stream comprising uncondensable components, such as oxygen and/or argon (said third stream not shown in FIG. 1). Still further, stream 3 may be subjected to hydrotreatment in a hydrotreater unit before entering ethylene oxide production unit 5 (said hydrotreater unit not shown in FIG. 1) to convert any acetylene present.

Figure 2:
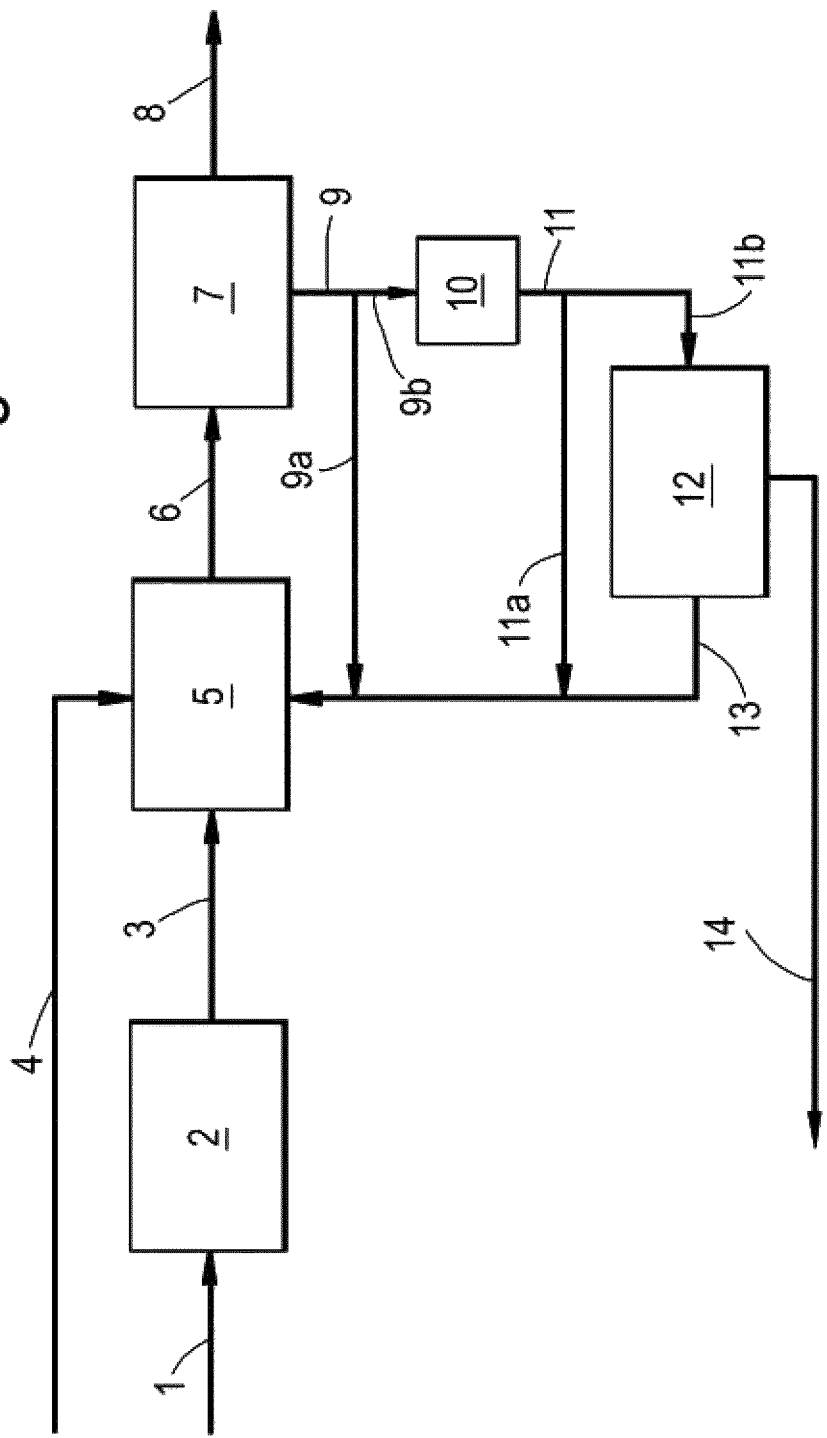
FIG. 2 shows a further schematic representation of an embodiment of the process according to the invention.

An embodiment of the present invention, wherein ethane from the stream comprising ethylene oxide, unconverted ethylene and ethane resulting from the step of producing ethylene oxide is not recycled to the ethylene production step but only to the ethylene oxide production step, is illustrated in FIG. 2. In the latter embodiment, ethane from the stream comprising ethylene oxide, unconverted ethylene and ethane is only recycled to the step of producing ethylene oxide. Such embodiment especially applies advantageously to cases where during ethylene production ethane is produced as a by-product, as for example in the above-mentioned methanol to ethylene conversion process.

For an explanation of the flow scheme of FIG. 2, reference is made to the above explanation of the flow scheme of FIG. 1, the only difference being that in the flow scheme of FIG. 2 stream 14 is not recycled to ethylene production unit 2.

In the ethylene oxide production step of the present process, ethylene oxide is produced by subjecting ethylene and ethane from the stream comprising ethylene and ethane, originating from the ethylene production step, to oxidation conditions resulting in a stream comprising ethylene oxide, unconverted ethylene and ethane.

An advantage of the present process is that the product stream resulting from the ethylene production step also comprises ethane, in addition to ethylene that is to be oxidized in the next step. Ethane is a suitable ballast gas in the oxidation of ethylene. As discussed above, normally nitrogen or methane is added as a ballast gas in the oxidation of ethylene. Now that in the present invention, ethane present in the ethylene containing product stream resulting from the ethylene production step functions as a ballast gas in the ethylene oxide production step, no or substantially less of a separate ballast gas, such as nitrogen or methane, has to be added. This results in a much simpler and more efficient ethylene oxidation process.

In the present invention, additional ballast gas, such as nitrogen or methane, may be added to the ethylene oxide production step. However, it is also envisaged in cases wherein ethylene is produced from a feed containing ethane in the ethylene production step of the present process, that the conversion in the ethylene production step is tuned depending on the desired amount of ballast gas needed in the ethylene oxide production step. That is to say, in case the demand for ballast gas in the ethylene oxide production step is relatively low, conversion in the ethylene production step may be set higher such that relatively less unconverted ethane is present in the product stream resulting from the ethylene production step. And, conversely, in case the demand for ballast gas in the ethylene oxide production step is relatively high, conversion in the ethylene production step may be set lower such that relatively more unconverted ethane is present in the product stream resulting from the ethylene production step. Alternatively, conversion in the ethylene production step may be kept constant and additional ballast gas, such as nitrogen or methane, may be added to the ethylene oxide production step, as mentioned above. For example, the conversion in the ethylene production step of the present process may range from 5 to 90%, suitably from 10 to 60%.

In the ethylene oxide production step of the present process, ethylene and ethane from the stream comprising ethylene and ethane are contacted with an oxidizing agent. The oxidizing agent may be high-purity oxygen or air, but is preferably high-purity oxygen which may have a purity greater than 90%, preferably greater than 95%, more preferably greater than 99%, and most preferably greater than 99.9%. Typical reaction pressures are 1-40 bar, suitably 10-30 bar, and typical reaction temperatures are 100-400° C., suitably 200-300° C.

Further, the amounts of ethylene and ethane, respectively, as fed to the ethylene oxide production step of the present process, may be of from 10 to 90 wt. %, suitably of from 20 to 80 wt. % of ethylene, and 90 to 10 wt. %, suitably of from 80 to 20 wt. % of ethane, respectively, all said amounts based on the total amount of the stream or the streams comprising ethylene and/or ethane as fed to said ethylene oxide production step.

The minimum amount of ethylene as referred to above may be 1 wt. %, 5 wt. %, 10 wt. %, 20 wt. %, 25 wt. %, 30 wt. % or 35 wt. %. The maximum amount of ethylene as referred to above may be 99 wt. %, 95 wt. %, 90 wt. %, 80 wt. %, 70 wt. %, 60 wt. %, 55 wt. %, 50 wt. % or 45 wt. %. The minimum amount of ethane as referred to above may be 1 wt. %, 5 wt. %, 10 wt. %, 20 wt. %, 25 wt. %, 30 wt. % or 35 wt. %. The maximum amount of ethane as referred to above may be 99 wt. %, 95 wt. %, 90 wt. %, 80 wt. %, 70 wt. %, 60 wt. %, 55 wt. %, 50 wt. % or 45 wt. %.

Further, it is preferred that in the ethylene oxide production step of the present process, the ethylene and ethane are contacted with a catalyst, preferably a silver containing catalyst. A typical reactor for the ethylene oxide production step consists of an assembly of tubes that are packed with catalyst. A coolant may surround the reactor tubes, removing the reaction heat and permitting temperature control.

In case a silver containing catalyst is used in the ethylene oxide production step of the present process, the silver in the silver containing catalyst is preferably in the form of silver oxide. Preferred is a catalyst comprising particles wherein silver is deposited on a carrier. Suitable carrier materials include refractory materials, such as alumina, magnesia, zirconia, silica and mixtures thereof. The catalyst may also contain a promoter component, e.g. rhenium, tungsten, molybdenum, chromium, nitrate- or nitrite-forming compounds and combinations thereof. Preferably, the catalyst is a pelletized catalyst, for example in the form of a fixed catalyst bed, or a powdered catalyst, for example in the form of a fluidized catalyst bed.

The nature of the ethylene oxidation catalyst, if any, is not essential in terms of obtaining the advantages of the present invention as described herein. The amount of the ethylene oxidation catalyst is neither essential. If a catalyst is used, preferably a catalytically effective amount of the catalyst is used, that is to say an amount sufficient to promote the ethylene oxidation reaction. Although a specific quantity of catalyst is not critical to the invention, preference may be expressed for use of the catalyst in such an amount that the gas hourly space velocity (GHSV) is of from 100 to 50,000 hr$^{-1}$, suitably of from 500 to 20,000 hr$^{-1}$, more suitably of from 1,000 to 10,000 hr$^{-1}$, most suitably of from 2,000 to 4,000 hr$^{-1}$.

In the present specification, "GHSV" or gas hourly space velocity is the unit volume of gas at normal temperature and pressure (0° C., 1 atmosphere, i.e. 101.3 kPa) passing over one unit volume of catalyst per hour.

A moderator, for example a chlorohydrocarbon such as monochloroethane (ethyl chloride), vinyl chloride or dichloroethane, may be supplied for catalyst performance control in the ethylene oxide production step of the present process. Most suitably, ethyl chloride is used.

Moderators that can be suitably used in the ethylene oxide production step of the present process are also disclosed in above-mentioned GB1314613, the disclosure of which is herein incorporated by reference. GB1314613 discloses the use of an inhibitor (that is to say, a moderator), selected from ethylene dichloride, vinyl chloride, dichlorobenzene, monochlorobenzene, dichloromethane, and chlorinated phenyls, chlorinated biphenyls and chlorinated polyphenyls, in the production of ethylene oxide from ethylene.

The nature of the moderator, if any, is not essential in terms of obtaining the advantages of the present invention as described herein. The amount of the moderator is neither essential. The amount of such moderator in the reaction mixture may range from 1 part per million by volume (ppmv) to 2 vol. %, suitably 1 to 1,000 ppmv. The minimum amount of moderator in the reaction mixture may be 0.1 ppmv, 0.2 ppmv, 0.5 ppmv, 1 ppmv, 2 ppmv, 5 ppmv, 10 ppmv or 50 ppmv. The maximum amount of moderator in the reaction mixture may be 2 vol. %, 1 vol. %, 1,000 ppmv, 800 ppmv or 700 ppmv.

A suitable range for the amount of moderator that can be used in the ethylene oxide production step of the present process is also disclosed in above-mentioned GB1314613 in relation to the above-mentioned group of specific inhibitors (that is to say, moderators) as disclosed in said GB1314613, the disclosure of which is herein incorporated by reference.

Examples of ethylene oxidation processes, including catalysts and other process conditions, are for example disclosed in US20090281345 and above-mentioned GB1314613, the disclosures of which are herein incorporated by reference. All of these ethylene oxidation processes are suitable for the ethylene oxidation step of the present invention.

In accordance with the present invention, the process for producing ethylene in the ethylene production step may be any process as long as it results in a stream comprising ethylene and ethane. One example of such process is a process for steam cracking hydrocarbon streams, such as an ethane stream, a naphtha stream, a gasoil stream or a hydrowax stream, into ethylene. The product stream resulting from such steam cracking process will always contain, in addition to the ethylene product, some unconverted ethane and/or ethane by-product.

In the present specification, "naphtha" refers to a mixture comprising saturated hydrocarbons which have a boiling point ranging from 20 to 200° C. Generally, said hydrocarbons have between 5 and 12 carbon atoms. Further, "gasoil" refers to a mixture comprising saturated hydrocarbons which have a boiling point ranging from 200 to 600° C., and "hydrowax" refers to a mixture comprising saturated hydrocarbons which have a boiling point ranging from 250 to 700° C.

The steam cracking process is performed at elevated temperatures, preferably in the range of from 650 to 1000° C., more preferably of from 750 to 950° C. The conversion is typically in the range of from 40 to 75 mol %, based on the total number of moles of hydrocarbon provided to the cracking zone. Hydrocarbon stream steam cracking processes are well known. Reference is for instance made to Kniel et al., Ethylene, Keystone to the petrochemical industry, Marcel Dekker, Inc, New York, 1980, in particular chapter 6 and 7.

Hereinbelow, the present invention and its advantages are further illustrated with reference to a process wherein the ethylene is produced by oxidative dehydrogenation (oxydehydrogenation; ODH) of ethane.

In one embodiment, the present invention relates to a process for the production of ethylene oxide, comprising the steps of:

producing ethylene by subjecting a stream comprising ethane to oxydehydrogenation conditions resulting in a stream comprising ethylene and unconverted ethane;

producing ethylene oxide by subjecting ethylene and unconverted ethane from the stream comprising ethylene and unconverted ethane to oxidation conditions resulting in a stream comprising ethylene oxide, unconverted ethylene and unconverted ethane; and recovering ethylene oxide from the stream comprising ethylene oxide, unconverted ethylene and unconverted ethane.

Preferably, in the above-mentioned ethane oxydehydrogenation embodiment, a stream comprising unconverted ethylene and unconverted ethane is separated from the stream comprising ethylene oxide, unconverted ethylene and unconverted ethane and is recycled to the step of producing ethylene oxide. Further, preferably, said separated stream comprising unconverted ethylene and unconverted ethane is further separated into a stream comprising unconverted ethylene which is recycled to the step of producing ethylene oxide and a stream comprising unconverted ethane which is recycled to the step of producing ethylene.

In addition, advantageously, the latter separation is not critical so that a complete separation of ethane from ethylene is not needed. In the ethane oxydehydrogenation embodiment of the present invention, ethane is both starting material in the ethylene production step and ballast gas in the subsequent ethylene oxide production step. All that matters is that the separated substream which comprises more ethylene than the other separated substream is recycled to the step of producing ethylene oxide, whereas the other separated substream is recycled to the step of producing ethylene.

Before recycle of said streams, carbon dioxide may be removed partially or completely, in a way as is for example discussed above with reference to FIGS. 1 and 2.

The flow schemes of FIGS. 1 and 2 are equally applicable to the ethane oxydehydrogenation embodiment of the present invention as described above, with the proviso that in the latter embodiment oxidizing agent should not only be fed to ethylene oxide production unit 5 but also to ethylene production unit 2 (the latter oxidizing agent feed is not shown in FIGS. 1 and 2).

The same advantages as described above apply to the ethane oxydehydrogenation embodiment of the present invention.

An additional advantage of the ethane oxydehydrogenation embodiment of the present invention is that there is no need to remove remaining oxidizing agent, if any, from the product stream resulting from the ethylene production step, because oxidizing agent is needed anyway in the subsequent production of ethylene oxide. For example, US20100256432 addresses the cumbersome requirement to eliminate unreacted oxygen from an ethane oxydehydrogenation product stream.

Figure 3:
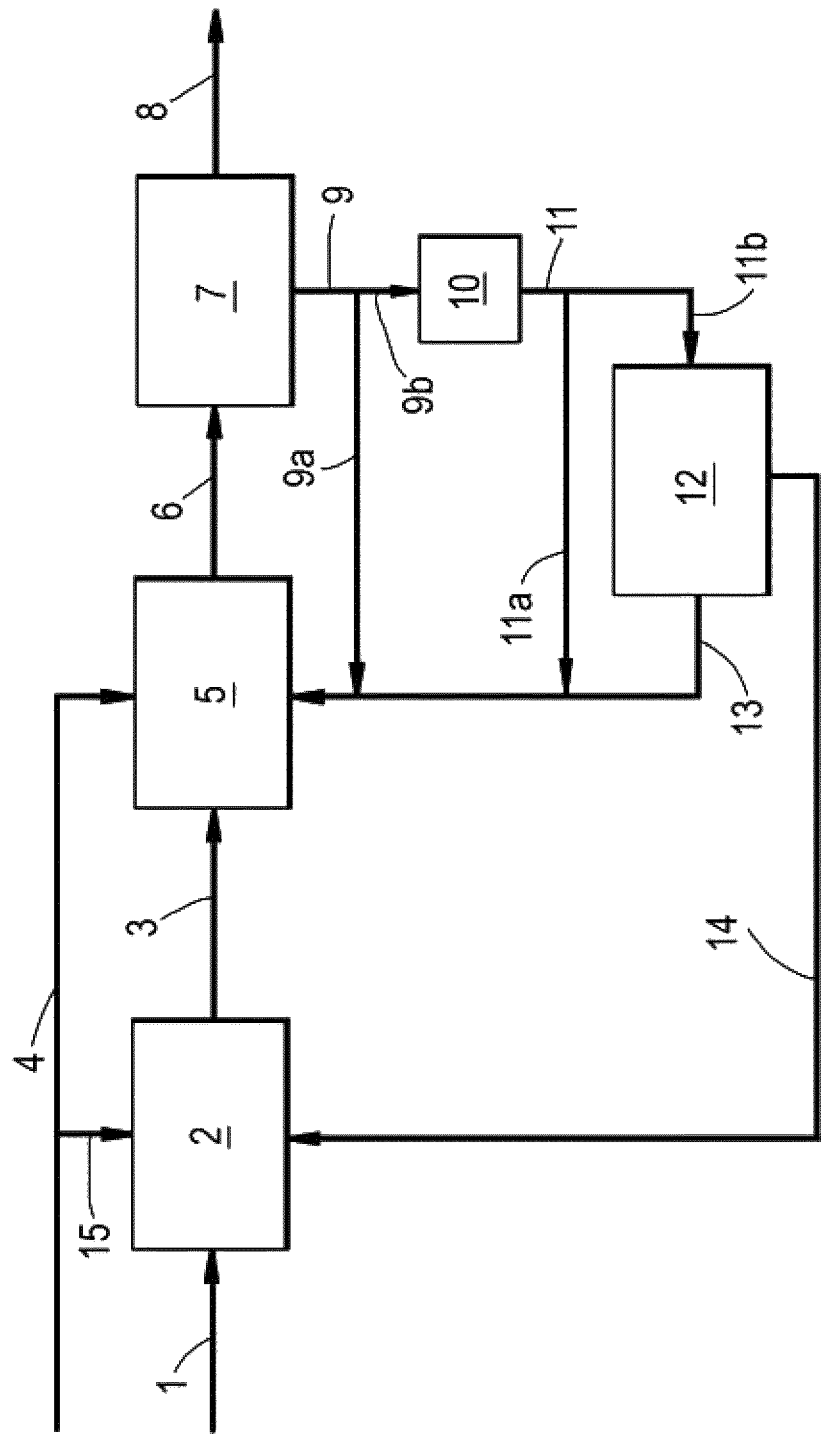
FIG. 3 shows a further schematic representation of an embodiment of the process according to the invention.

Further, advantageously, the same source of oxidizing agent as used for feeding oxidizing agent to the ethylene oxide production step of the present process, can be used for feeding oxidizing agent to the ethylene production step of the ethane oxydehydrogenation embodiment of the present process. This is illustrated in FIG. 3. For an explanation of the flow scheme of FIG. 3, reference is made to the above explanation of the flow scheme of FIG. 1, the only difference being that in the flow scheme of FIG. 3 there is an additional stream 15 comprising an oxidizing agent which is fed to ethylene production unit 2 and which originates from the same source used for stream 4 comprising an oxidizing agent which is fed to ethylene oxide production unit 5.

In the ethylene production step of the above-mentioned ethane oxydehydrogenation embodiment of the present invention, a stream comprising ethane is contacted with an oxidizing agent, thereby resulting in oxidative dehydrogenation of the ethane into ethylene. The oxidizing agent may be high-purity oxygen or air, but is preferably high-purity oxygen which may have a purity greater than 90%, preferably greater than 95%, more preferably greater than 99%, and most preferably greater than 99.9%.

Further, it is preferred that the stream comprising ethane is contacted with a catalyst. The catalyst may be a metal oxide catalyst, preferably a mixed metal oxide catalyst which is a metal oxide catalyst containing two or more different metals, preferably at most four or five different metals. Preferably, the catalyst is a pelletized catalyst, for example in the form of a fixed catalyst bed, or a powdered catalyst, for example in the form of a fluidized catalyst bed.

Examples of ethane oxydehydrogenation processes, including catalysts and other process conditions, are for example disclosed in U.S. Pat. No. 7,091,377, WO2003064035, US20040147393, WO2010096909 and above-mentioned US20100256432, the disclosures of which are herein incorporated by reference.

A suitable ethane oxydehydrogenation catalyst is a mixed metal oxide catalyst containing molybdenum, vanadium, tellurium and niobium as the metals, which may have the following formula:

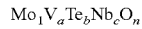

$$Mo_1V_aTe_bNb_cO_n$$

wherein a is from 0.01 to 1, b is from >0 to 1, c is from >0 to 1, and n is a number which is determined by the valency and frequency of elements other than oxygen. The nature of the ethane oxydehydrogenation catalyst is not essential in terms of obtaining the advantages of the present invention as described herein.

The amount of the ethane oxydehydrogenation catalyst, if any, is neither essential. If a catalyst is used, preferably a catalytically effective amount of the catalyst is used, that is to say an amount sufficient to promote the ethane oxydehydrogenation reaction. Although a specific quantity of catalyst is not critical to the invention, preference may be expressed for use of the catalyst in such an amount that the gas hourly space velocity (GHSV) is of from 100 to 50,000 $hr^{-1}$, suitably of from 200 to 20,000 $hr^{-1}$, more suitably of from 300 to 10,000 $hr^{-1}$, most suitably of from 500 to 5,000 $hr^{-1}$.

In the ethane oxydehydrogenation embodiment of the present invention, typical reaction pressures are 0.1-20 bar, suitably 1-10 bar, and typical reaction temperatures are 100-600° C., suitably 200-500° C.

In general, the product stream resulting from the ethylene production step in the ethane oxydehydrogenation embodiment of the present invention comprises water in addition to ethylene and unconverted ethane. Water may easily be separated from said product stream, for example by cooling down the product stream from the reaction temperature to a lower temperature, for example room temperature, so that the water condenses and can then be separated from the product stream.

Preferably, water is separated from the product stream resulting from the ethylene production step in the ethane oxydehydrogenation embodiment of the present invention, and the resulting product stream is then sent directly to the next step, that is to say the ethylene oxidation step. In this way, advantageously there is not any intermediate step, other than said water removal. Therefore, there is no need to separate ethylene from unconverted ethane and/or to remove any carbon monoxide or carbon dioxide prior to the ethylene oxidation step.

Preferably, at least part of the ethylene oxide is converted to monoethylene glycol (MEG), which is a useful liquid product. The conversion of ethylene oxide to MEG may be done using any MEG producing process that uses ethylene oxide. Typically the ethylene oxide is hydrolysed with water to MEG. Optionally, the ethylene oxide is first converted with carbon dioxide to ethylene carbonate, which is subsequently hydrolysed to MEG and carbon dioxide. The water is provided to the MEG zone as a feed containing water, preferably pure water or steam. The MEG product is obtained from the MEG zone as a MEG-comprising effluent. Suitable processes for the production of ethylene oxide and MEG are described for instance in US2008139853, US2009234144, US2004225138, US20044224841 and US2008182999, the disclosures of which are herein incorporated by reference.

The invention is further illustrated by the following Example.

Example

In this experiment, ethylene was oxidized into ethylene oxide (EO) over a rhenium-containing catalyst prepared according to US20090281345 and having a silver content of 17.5 wt. %, using air as a source of oxygen (oxidizing agent), using ethane as ballast gas, and using ethyl chloride (EC) as moderator.

The experiment was performed in a "single-pass" or "once-through" mode without any recycle. An inlet gas stream was contacted with the catalyst in a U-shaped tubular steel microreactor that was immersed in a temperature-controlled molten metal bath. The inlet gas stream comprised 25 vol. % of ethylene, 8.3 vol. % of oxygen, 0.6 vol % of carbon dioxide, 260 parts per million by volume (ppmv) of EC, 32.3 vol. % of ethane, the balance comprising nitrogen originating from the air that was used as the source of oxygen and from the blend containing EC that was used as the moderator.

A gas flow rate of 254 cc/minute was directed through a 4.6 g charge of catalyst, providing a gas hourly space velocity (GHSV) of 2,850 hr$^{-1}$. Total pressure was 16.5 bar gauge. Generation of 3.48 vol. % EO in the product stream corresponded to a work rate of 195 kg of product per cubic meter of catalyst bed per hour (kg/m$^3$/hr). The catalyst temperature to achieve said target work rate was 244° C.

Results of the experiment are shown in Table 1 below. The experiment shows that ethane can be used as a ballast gas in the oxidation of ethylene to EO. In addition, when using ethane as ballast gas, the selectivity of the ethylene oxidation reaction to EO is high. Furthermore, ethane is converted to only a small extent.

TABLE 1

| | |
|---|---|
| Oxygen conversion | 46.6% |
| Ethylene conversion | 15.2% |
| Ethane conversion | 0.7% |
| Selectivity of conversion of ethylene to EO | 88.9% |

What is claimed is:

1. A process for producing ethylene oxide, comprising the steps of:
producing ethylene by subjecting a stream comprising ethane to oxydehydrogenation conditions resulting in a stream comprising ethylene and unconverted ethane;
producing ethylene oxide by subjecting ethylene and unconverted ethane from the stream comprising ethylene and unconverted ethane to oxidation conditions resulting in a stream comprising ethylene oxide, unconverted ethylene and unconverted ethane; and
recovering ethylene oxide from the stream comprising ethylene oxide, unconverted ethylene and unconverted ethane.

2. A process according to claim 1, wherein a stream comprising unconverted ethylene and unconverted ethane is separated from the stream comprising ethylene oxide, unconverted ethylene and unconverted ethane and is recycled to the step of producing ethylene oxide.

3. A process according to claim 1, wherein a stream comprising unconverted ethylene and unconverted ethane is separated from the stream comprising ethylene oxide, unconverted ethylene and unconverted ethane, the stream comprising unconverted ethylene and unconverted ethane is separated into a stream comprising unconverted ethylene which is recycled to the step of producing ethylene oxide and a stream comprising unconverted ethane which is recycled to the step of producing ethylene.

4. A process according to claim 1, wherein at least part of the ethylene oxide is converted to monoethylene glycol.

5. A process according to claim 1, wherein the stream comprising ethylene and unconverted ethane further comprises carbon monoxide or carbon dioxide.

6. A process according to claim 1, wherein the stream comprising ethylene and unconverted ethane further comprises water and wherein water is separated from the stream comprising ethylene and unconverted ethane prior to subjecting ethylene and unconverted ethane from the stream comprising ethylene and unconverted ethane to oxidation conditions.

* * * * *